United States Patent
Díaz et al.

(10) Patent No.: US 7,820,637 B2
(45) Date of Patent: Oct. 26, 2010

(54) USE OF 5'-METHYLTHIOADENOSINE (MTA) IN THE PREVENTION AND/OR TREATMENT OF AUTOIMMUNE DISEASES AND/OR TRANSPLANT REJECTION

(75) Inventors: Pablo Villoslada Díaz, Navarra (ES); Matías Ávila Zaragoza, Navarra (ES); Beatriz Moreno Bruna, Navarra (ES); Fernando Corrales Izquierdo, Navarra (ES); Carmen Berasain Lasarte, Navarra (ES); Elena Ruiz García-Trevijano, Navarra (ES)

(73) Assignee: Proyecto de Biomedicina Cima, S.L., Pamplona (ES)

( * ) Notice: Subject to any disclaimer, the term of this patent is extended or adjusted under 35 U.S.C. 154(b) by 115 days.

(21) Appl. No.: 11/908,697

(22) PCT Filed: Mar. 17, 2005

(86) PCT No.: PCT/ES2005/000139

§ 371 (c)(1),
(2), (4) Date: Dec. 20, 2007

(87) PCT Pub. No.: WO2006/097547

PCT Pub. Date: Sep. 21, 2006

(65) Prior Publication Data

US 2009/0042831 A1 Feb. 12, 2009

(51) Int. Cl.
*A61K 31/70* (2006.01)
*C07H 19/167* (2006.01)
(52) U.S. Cl. ........................ 514/45; 536/27.3
(58) Field of Classification Search .................. None
See application file for complete search history.

(56) References Cited

U.S. PATENT DOCUMENTS 6,555,518 B1  4/2003  Margreiter et al.

FOREIGN PATENT DOCUMENTS

| EP | 0352609 | 1/1990 |
| GB | 2074446 | 11/1981 |
| WO | 9816184 | 4/1998 |
| WO | 03028712 | 4/2003 |

OTHER PUBLICATIONS

Hevia et al., "5'-Methylthioadenosine Modulates the Inflammatory Response to Endotoxin in Mice and in Rat Hepatocytes," Hepatology, vol. 39, No. 4, (2004), pp. 1088-1098.
Mowen et al., "Arginine Methylation of NIP45 Modulates Cytokine Gene Expression in Effector T Lymphocytes," Molecular Cell, vol. 15, (Aug. 27, 2004), pp. 559-571.
Cohen, Philip L., Systemic Autoimmunity, Fundamental Immunology, W. E. Paul (ed.), 5th edition, 2003, pp. 1371-1399, Chapter 44.
Davidson, Anne., M.B., B.S., et al., Autoimmune Diseases, New England Journal of Medicine, 2001, pp. 340-350, vol. 345, No. 5.
Janeway, C., et al., Autoimmunity: responses to self antigens, Immunobiology, 2004, 6th Ed., Garland Publ. Inc., New York.
Rosenberg, Helene F., et al., Inflammation, Fundamental Immunology, W.E. Paul (ed.) 5th edition, 2003, pp. 1151-1169.
Liu, Eric H., et al., T cell-directed therapies: lessons learned and future prospects, Nature Immunology, 2007, pp. 25-30, vol. 8, No. 1.
Santana, Maria Angelica, et al., Cell Biology of T Cell Activation and Differentiation, International Review of Cytology, 2006, pp. 217-274, vol. 250.

*Primary Examiner*—Lawrence E Crane
(74) *Attorney, Agent, or Firm*—Tristan A. Fuierer; Moore & Van Allen, PLLC; Andrew D. Gerschutz (57) ABSTRACT

5'-methylthioadenosine (MTA), its pharmaceutically acceptable salts and/or prodrugs may be used in the prevention and/or treatment of autoimmune diseases, such as, for example, Multiple Sclerosis (MS), as well as in the prevention and/or treatment of transplant rejection.

7 Claims, 4 Drawing Sheets

USE OF 5'-METHYLTHIOADENOSINE (MTA) IN THE PREVENTION AND/OR TREATMENT OF AUTOIMMUNE DISEASES AND/OR TRANSPLANT REJECTION

CROSS-REFERENCE TO RELATED APPLICATIONS

This application is filed under the provisions of 35 U.S.C. §371 and claims the priority of International Patent Application No. PCT/ES2005/000139 on Mar. 17, 2005, entitled "Use of 5'-Methylthioadenosine (MTA) in the Prevention and/or Treatment of Autoimmune Diseases and/or Transplant Rejection" in the name of Pablo Villoslada Diaz, et al.

FIELD OF THE INVENTION

The invention is related, in general, with the use of 5'-methylthioadenosine (MTA), its pharmaceutically acceptable salts and/or prodrugs in the prevention and/or treatment of autoimmune diseases, as well as in the prevention and/or treatment of transplant rejections and, in particular, in the prevention and/or treatment of Multiple Sclerosis (MS).

BACKGROUND OF THE INVENTION

Autoimmune diseases are serious diseases, which cause significant health and personal problems and currently represent the fourth most important health problem in industrialised countries. As an example, Multiple Sclerosis (MS) is an autoimmune disease with great healthcare relevance that causes significant sequelae. Similarly, transplant rejection, a specific case of autoimmunity in which the activation of transplant antigen-specific T lymphocytes leads to their elimination, represents a serious complication for those patients receiving transplants, with a high personal and social cost.

Due to their particular characteristics (mechanisms and response to treatments), autoimmune diseases form a specific sub-group within inflammatory diseases. As is well-known, inflammatory diseases are those in which innate inflammation predominates or in which the treatment is designed to fight the innate inflammation. However, autoimmune diseases are different from inflammatory diseases in that inflammation by adaptive immunity (lymphocytes) predominates; consequently, classical anti-inflammatory treatments, aimed at modulating the innate inflammation, are not effective in the treatment of autoimmune diseases, seemingly due to the fact that, in order to control the chronic activity of an autoimmune disease it is necessary, in addition to suppressing the local inflammation, to modulate lymphocyte activity by means of immunomodulators.

The treatment of autoimmune diseases is a serious problem, since many therapies are symptomatic and those therapies which modify the course of the disease have partial effectiveness and side-effects, as well as significant costs. The control of autoimmune diseases is based, in general, on the modulation of T lymphocyte activation by means of immunosuppressant or immunomodulatory therapies; for this reason, the classical anti-inflammatory therapies are ineffective.

Currently, in treating autoimmune diseases and transplant rejection, three types of therapies tend to be used, all of them centred on limiting the activation and effect of autoreactive T lymphocytes:

a) on the one hand, the administration of corticoids (e.g. prednisone, 5'-methylprednisone, dexamethasone and ACTH, amongst others), either orally, subcutaneously or intravenously and in the form of boluses, for short periods of time or indefinitely, may alleviate some of these diseases, albeit always in a partial manner and with significant long-term secondary effects which limit their use;

b) on the other hand, the administration of immunosuppressants (e.g. cyclophosphamide, mitoxantrone, methrotrexate, azathioprine and cyclosporin A, amongst others), orally or intravenously, improves the control of many of these diseases, albeit with potentially serious or even lethal side-effects, which greatly limit their use; and c) on the other hand, the administration of immunomodulators (e.g. interferon-beta, interferon-alpha, glatiramer acetate, anti-CD20 or anti-TNFa monoclonal antibodies, amongst others) improves the control of these diseases, albeit in a partial manner, with habitual side-effects and with a high cost since they are biotechnological products.

Therefore, it would of great interest to have a new treatment available that is effective in preventing lymphocyte activation and that prevents or reduces the activity of autoimmune diseases and transplant rejection, with limited secondary effects.

It has now been found that 5'-methylthioadenosine (MTA) may be used in the prevention and/or treatment of autoimmune diseases, as well as in the prevention and/or treatment of transplant rejection and, specifically, in the prevention and/or treatment of Multiple Sclerosis (MS).

MTA is a hydrophobic adenine sulphur-nucleoside, in which the hydroxyl group in the 5' position of the ribose is replaced by a methylthio group. MTA is found in low proportions in all cellular types, including prokaryotes, yeasts, plants and higher eukaryotes, and it has been observed that it is naturally present in all mammal tissues. MTA is a well-known molecule that has very diverse properties for cancer control, as well as for regeneration and innate inflammation.

U.S. Pat. No. 4,454,122 discloses the use of MTA as an anti-inflammatory, analgesic and anti-pyretic agent; specifically, the use of MTA in the treatment of innate inflammation. The anti-inflammatory activity is analysed by means of the suppression of the innate immune response in edema, pleuritis and foreign-body granuloma models. The role of MTA in the suppression of lymphocyte activation is not analysed, nor is its role as an immunomodulator in autoimmune diseases or transplant rejection.

The effects of MTA on cancer have also been studied. It has been extensively observed that MTAP (5'-methylthioadenosine phosphorylase) activity is lacking in many malignant cells, and that, in culture, these MTAP-deficient cells secrete MTA instead of metabolising it. As an example, international patent application WO2004/074325 discloses the use of compounds which inhibit the MTAP enzyme in cancer treatment. In experimental models of chemically-induced hepatocarcinogenesis, in which it has been observed that MTA levels are reduced, the administration of MTA induces a dose-dependent inhibition of liver pre-neoplastic lesions and DNA synthesis.

On the other hand, the function and proliferation of T lymphocytes seems to be particularly sensitive to inhibition by MTA. This compound inhibits, in a reversible, non-toxic and dose-dependent manner, the proliferation of mitogen-stimulated murine lymphoid cell lines and human peripheral lymphocytes. Amongst the MTA effects which may interfere with cell proliferation, one can cite the inhibition of protein methylation or the inhibition of phosphodiesterase activity. The authors of the invention themselves proclaimed, in a conference paper titled "*A Methylation-Inhibitor Suppresses*

T Cell Activation and Prevents Experimental Autoimmune Encephalomyelitis", in the 7th Meeting of the International Society of Neuroimmunology, Venice, September 2004 [Abstract published in the Journal of Neuroimmunology 2004, Vol. 154, numbers 1-2, page 85], the utility of MTA as a potent inhibitor of methylation reactions, which prevents the development of an autoimmune response in an animal model of Experimental Autoimmune Encephalomyelitis (EAE), consisting of Lewis rats immunised with myelin basic protein (MBP).

SUMMARY OF THE INVENTION

It has now been found, surprisingly, that MTA is capable of exerting a modulatory effect on T lymphocyte activation, which makes it capable of modifying inflammation in autoimmune diseases and transplant rejection, and, therefore, may be used in the prevention and/or treatment of autoimmune diseases, as well as in the prevention and/or treatment of transplant rejection and, particularly, in the prevention and/or treatment of MS. In this regard, in this invention MTA acts as an immunomodulatory agent since its effect is specifically exerted on lymphocytes.

This new application of MTA is based on research conducted by the inventors on animal models of acute EAE and chronic-recurrent EAE, to whom MTA was administered; it was observed that those animals that had been treated with MTA either did not exhibit any clinical signs of the disease or else, once the disease had already appeared, exhibited a significant attenuation during the course of the disease.

Therefore, in an aspect, the invention relates to the use of MTA in the preparation of a medication designed for (i) the prevention and/or treatment of an autoimmune disease or (ii) for the prevention and/or treatment of a transplant rejection. In a specific embodiment, this autoimmune disease is MS.

In another aspect, the invention relates to a method for the prevention and/or treatment of an autoimmune disease in an individual suffering from an autoimmune disease, which comprises the administration of a therapeutically effective quantity of MTA to said individual. In a specific embodiment, this autoimmune disease is MS.

In another aspect, the invention relates to a method for the prevention and/or treatment of transplant rejection in an individual receiving a transplant or who is going to receive a transplant, which comprises the administration of a therapeutically effective quantity of MTA to said individual.

The use of MTA in the prevention and/or treatment of autoimmune diseases, specifically MS, and transplant rejection represents an effective way to avoid the problems posed by current therapeutic strategies, such as the long-term secondary effects of the corticoids, immunosuppressants and immunomodulators used in the treatment of autoimmune diseases and transplant rejection.

DETAILED DESCRIPTION OF THE INVENTION

In one respect, the invention relates to the use of MTA, its pharmaceutically acceptable salts and/or prodrugs, in the preparation of a medicament designed for (i) the prevention and/or treatment of an autoimmune disease or (ii) for the prevention and/or treatment of transplant rejection.

As used herein, the term "pharmaceutically acceptable salts" refers to any MTA salt that may be used in the preparation of a medicament. The nature of the salt is not critical, provided that it is pharmaceutically acceptable. Amongst the pharmaceutically acceptable salts of MTA are acid addition salts, which may be obtained from organic or inorganic acids, by conventional methods well-known to those skilled in the art, by making the appropriate acid react with MTA in the adequate stoichiometric quantity. Illustrated examples of acids which may be used to obtain these acid addition salts include, but are not limited thereto, organic acids, such as, for example, ascorbic acid, citric acid, 1,4-butanedisulfonic acid, p-toluenesulfonic acid, etc., or inorganic acids, such as, for example, hydrochloric acid, sulphuric acid, etc. As an illustration, for example, MTA hydrochloride may be used in injectable formulations; MTA hydrochloride, MTA sulphate, MTA citrate, MTA ascorbate, MTA 1,4-butanedisulfonate (enteric coated tablets), MTA p-toluenesulfonate, etc. may be used in oral formulations.

Moreover, the scope of this invention includes MTA prodrugs. The term "prodrug", as used herein, includes any compound derived from MTA, for example, ester, amide, etc., which, upon being administered to an individual, is capable of providing MTA, directly or indirectly, to said individual. Preferably, said derivative is a compound that increases the bioavailability of MTA when administered to an individual or that promotes the release of MTA in a biological compartment. The nature of said derivative is not critical, provided that it may be administered to an individual and that it provides MTA in an individual's biological compartment. The preparation of said prodrug may be performed by conventional methods known by those skilled in the art.

MTA is a commercial product that can be supplied by the Sigma company. Alternatively, said compound may be obtained by known methods, for example, starting from S-adenosylmethionine (SAM), following the procedure described by Schlenk, F. et al., Arch. Biochem. Biophys., 1964, 106:95-100, as mentioned in the Example that accompanies this description.

For its administration in the prevention and/or treatment of an autoimmune disease, such as MS, or in the prevention and/or treatment of a transplant rejection, MTA, its pharmaceutically acceptable salts and/or prodrugs, shall be formulated in an appropriate pharmaceutical composition, in the therapeutically effective quantity, jointly with one or more pharmaceutically acceptable carriers, adjuvants or excipients.

Examples of pharmaceutical compositions include any solid (e.g. tablets, capsules, granules, etc.) or liquid composition (e.g. solutions, suspensions, emulsions, etc.) to be administered by any appropriate route, for example, oral, subcutaneous, intraperitoneal, intravenous, etc.; typically, by oral route due to the chronic nature of the disease that is to be treated.

In a specific embodiment, said pharmaceutical compositions may be in an oral administration pharmaceutical form, either in solid or liquid form. Examples of oral administration pharmaceutical forms include tablets, capsules, granulates, solutions, suspensions, etc., and may contain the conventional excipients, such as bonding, diluent, disintegrating, lubricant, wetting, etc., excipients, and may be prepared by conventional methods. The pharmaceutical compositions may also be adapted for parenteral administration, in the form of, for example, solutions, suspensions or sterile, lyophilised products, in the appropriate dosage form; in this case, said pharmaceutical compositions shall include the adequate excipients, such as buffers, surfactants, etc. In any event, the excipients shall be selected on the basis of the selected administration of the pharmaceutical form. A review of the different pharmaceutical forms for drug administration and their preparation may be found in the book "Tratado de Farmacia Galénica", de C. Faulí i Trillo, 10th Edition, 1993, Luzán 5, S. A. de Ediciones.

For its application in therapy, the MTA shall preferably be in a pharmaceutically acceptable or substantially pure form, i.e. the MTA shall have a pharmaceutically acceptable purity level, excluding the pharmaceutically acceptable excipients and not including material considered to be toxic at normal dosage levels. The MTA purity levels are preferably above 50%, more preferably, above 70%, more preferably, above 90%. In a preferred embodiment, they are above 95% MTA.

In general, the therapeutically effective quantity of MTA to be administered shall be dependent, amongst other factors, on the individual who is to be treated, the severity of the disease suffered by the individual, the selected form of administration, etc. For this reason, the doses mentioned in this invention shall be considered solely as guides for those skilled in the art, and the latter shall adjust the doses on the basis of said variables. However, MTA may be administered one or more times a day, for example, 1, 2, 3 or 4 times a day, in a typical total daily quantity between 25 and 75 mg/kg/day.

MTA, its pharmaceutically acceptable salts and/or prodrugs, and the pharmaceutical compositions that contain them may be used jointly with other additional drugs that are useful in the prevention and/or treatment of autoimmune diseases or transplant rejection, for example, corticoids, immunosuppressants, immunomodulators, etc., in order to provide combination therapy. Said additional drugs may form a part of the same pharmaceutical composition or, alternatively, may be provided in the form of a separate composition for simultaneous or non-simultaneous administration with the pharmaceutical composition comprising MTA, or a prodrug or a pharmaceutically acceptable salt thereof.

As used herein, "autoimmune disease" is a disease that responds to the triggering of aggressive mechanisms in the patient's defences (immune system) against his/her own body's tissues. More specifically, autoimmune diseases are characterised in that inflammation by adaptive immunity (also called specific or acquired immunity) predominates, where the immunity is stimulated following exposure to infectious agents, and that its main components are lymphocytes. A list of autoimmune diseases may be found at the web site of the American Autoimmune Related Diseases Association [http://www.aarda.org]. Examples of autoimmune diseases include, but are not limited to: MS, Crohn's disease, rheumatoid arthritis, type 1 diabetes mellitus, psoriasis, lupus, ulcerous colitis, vitiligo, coeliac disease, vasculitis, dermatomyositis, polymyositis, thyroiditis (Hashimoto, Graves), myasthenia gravis, Guillain-Barre syndrome, uveitis, flat lichen, temporal arteritis, sarcoidosis, dry syndrome (Sjöegren), bronchial asthma, pemphigus, ankylosing spondilitis, sclerodermia, fibromyalgia, rheumatic fever, etc.

In a specific embodiment, the invention is intended for the use of MTA, its pharmaceutically acceptable salts and/or prodrugs, in the preparation of a medicament designed for the prevention and/or treatment of MS, specifically, in the treatment of MS, and, more specifically, in the prevention and/or treatment of MS in the delay of the appearance of subsequent outbreaks or in the progression of the disease (progressive phase) in an individual suffering from MS, i.e. after MS has already started. Trials conducted by the inventors have shown, in addition to MTA's preventive effect on the development of autoimmunity observed in the prevention of EAE in Lewis rats immunised with MBP (acute EAE model), that MTA also has a healing effect on chronic autoimmunity, since treatment with MTA improved the clinical symptoms and survival when the disease (MS) had already started, as has been verified in the CR-EAE model with DA rats immunised with rMOG. This aspect is highly significant since, currently, immunomodulatory therapies can only be used once the disease has already started, it being impossible to conduct preventive treatment since there are no pre-symptomatic markers.

In another specific embodiment, the invention relates to the use of MTA, its pharmaceutically acceptable salts and/or prodrugs in the preparation of a medicament designed for the prevention and/or treatment of transplant rejection. MTA, its pharmaceutically acceptable salts and/or prodrugs may be used to prevent and/or treat the rejection of practically any transplant. Examples of such transplants include, but are not limited thereto: kidney, liver, heart, lung, intestine, hematopoietic and bone marrow, skin, limbs, cornea, pancreas, stem cells and cell therapy, grafts or biomaterials, etc.

In another aspect the invention relates to a method for the prevention and/or treatment of an autoimmune disease in an individual suffering from an autoimmune disease, which comprises the administration of a therapeutically effective quantity of MTA, or of one of its pharmaceutically acceptable salts and/or prodrugs, to said individual. The autoimmune diseases that may be treated have been defined above, as have the characteristics of administration, pharmaceutical composition and therapeutically effective quantity of MTA. In a specific embodiment, said autoimmune disease is MS. MTA, its pharmaceutically acceptable salts and/or prodrugs may, in a specific embodiment, be used to delay the appearance of subsequent outbreaks in an individual suffering from MS or to delay the progression of MS (progressive phase) in an individual suffering from MS.

In another aspect, the invention relates to a method for the prevention and/or treatment of transplant rejection in an individual who is going to receive a transplant or who has received a transplant, which comprises the administration of a therapeutically effective quantity of MTA, or of one of its pharmaceutically acceptable salts and/or prodrugs, to said individual. Examples of transplants, not limited thereto, the rejection whereof may be prevented or treated with MTA, its pharmaceutically acceptable salts and/or prodrugs have already been mentioned, as have the characteristics of administration, pharmaceutical composition and therapeutically effective quantity of MTA. Said pharmaceutical composition may be administered either before or after the transplant (i.e. for prophylactic or therapeutic purposes) or else before and after the transplant, even if there are initially no symptoms of rejection (i.e. for prophylactic purposes).

As used herein, the term "individual" refers to any mammal and includes, but is not limited to, pets, rodents, primates and humans. Preferably, said individual is a human being, male or female, of any age or race.

In a specific embodiment of the invention, the administration of MTA is conducted alone or in combination with other therapies or with other drugs, in the form of combination therapy.

The following example illustrates the invention and should not be considered to limit the scope thereof.

EXAMPLE

Since the 1970s, it was believed that the acute Experimental Autoimmune Encephalomyelitis (EAE) model was a model for Multiple Sclerosis (MS) and that, therefore, effective treatments for acute EAE would also be effective for MS. However, hundreds of compounds have been tried which have been effective in treating acute EAE but not MS (Hohlfeld R. & Wekerle H. Proceeding National Academy of Sciences USA, October 2004, Vol. 101, Suppl. 2, page 14, 599, heading: MS and EAE, paragraph 3). In light of this, in addition to demonstrating effectiveness in the prevention of acute EAE, it is necessary to demonstrate effectiveness in the healing of chronic-relapsing EAE (a model for MS in general). In this regard, in this Example two non-human animal models have been used to demonstrate the effectiveness of MTA in the treatment of autoimmune diseases and, in particular, MS; specifically, (i) acute EAE in Lewis rats immunised with MBP [model for the outbreak of MS and for Acute Disseminated Encephalomyelitis (ADE)] and (ii) chronic-recurrent EAE (CR-EAE) in Dark Agouti (DA) rats immunised with MOG [model for MS].

I. Materials and Methods

Animals

For the model for acute EAE generated by immunisation with myelin basic protein (MBP), 6-8-week-old, 175-200-gram, Charles River female Lewis rats were used.

For the model for chronic-recurrent EAE generated by immunisation with oligodendrocyte glycoprotein (MOG), Dark Agouti (DA) rats were used, with an approximate weight of 200 grams.

The animals were housed in plastic cages in a room with natural lighting and they were supplied with food and water on a daily basis.

EAE Induction and Score

The Lewis rats were immunised with 100 μl of an emulsion containing saline solution and incomplete Freund's adjuvant (IFA) with 75 μg of MBP (fragment 68-82 of guinea pig myelin basic protein (Sigma), in equal volumes, and supplemented with 4 mg/ml of *Mycobacterium tuberculosis* H37RA (Difco). The immunisation was performed at the base of both hind legs.

The DA rats were immunised with 100 μl of an emulsion containing saline solution and incomplete Freund's adjuvant (IFA) with 75 μg of rMOG [Villoslada, P., et al., J. Exp Med, 2000. 191 (10):1799-806] (purified in our laboratory) at equal volumes and also supplemented with 4 mg/ml of *Mycobacterium tuberculosis*. The immunisation was performed on the base of both hind legs, as in the case of the Lewis rats.

The animals were weighed and the clinical symptoms of EAE were inspected on a daily basis by a treatment-blind evaluator. The severity of EAE was measured by means of the following scale: 0=normal; 1=flaccid tail; 2=slight paraparesis of the hind legs, unstable locomotion; 3=paraplegia; 4=tetraparesis; 5=death.

Treatments

The Lewis rats immunised with MBP were randomly divided into 2 groups. One of the groups was treated with MTA (100 μM concentration) at a dose of 4.3 mg/animal (equivalent to 28.6 μg/kg body weight). The MTA was synthesised from SAM (Europharma, Madrid (Spain)), following the procedure described by Schlenk F. et al., Arch. Biochem. Biophys., 1964, 106:95-100, at the Division of Hepatology and Gene Therapy of the Department of Internal Medicine, CIMA, University of Navarra, reconstituted in 10% dimethylsulfoxide (DMSO), and the other placebo group was treated with physiological serum and 10% DMSO by intraperitoneal injection (i.p.) on a daily basis after immunisation.

The DA rats immunised with rMOG were also randomly divided into two groups, one of which was treated with 100 μM MTA reconstituted in 300 mM Tris pH=7.8, and the other placebo group was treated solely with 300 mM Tris. The treatments began on day 15 after immunisation and were supplied on a daily basis by means of i.p. injection. The scores were blindly evaluated during the entire course of the disease.

Tissue Samples

The two Lewis rat groups were anaesthetised and injected by intracardiac route with 4% paraformaldehyde in 0.1 M phosphate buffer (pH 7.6) on day 16 of the disease. The brains and the cervical, thoracic and lumbar spinal cord segments were extracted and fixated for the entire night at 4° C. After fixation, the tissues were soaked in paraffin for histopathology and immunohistochemistry.

The two DA rat groups were also anaesthetised and injected following the same protocol on day 35 after immunisation. The tissues were also treated in the same manner for the histopathology and immunohistochemistry studies.

Spleen, liver and blood samples were also obtained from each animal. The spleens and the livers were quickly frozen in liquid nitrogen and kept in fragments at −80° C. in order to be able to conduct the studies with RT-PCR (reverse transcription and polymerase chain reaction). The blood was centrifuged at 800 rpm for 10 minutes in order to obtain the serum, which was kept at −80° C.

RNA Isolation and cDNA Synthesis

The spleen and liver tissue segments were homogenised in RNA lysis buffer with 2% β-mercaptoethanol using a manual homogeniser. The total RNA was extracted using the Rneasy Mini Kit (Quiagen), following the manufacturer's instructions. During RNA purification, the DNA was eliminated by treatment with DNase. The RNA concentration and purity was determined by measuring the absorbance at 260 nm and 280 nm with a spectrophotometer (Eppendorf). Reverse transcription of the total RNA was performed using the High Capacity cDNA Archive Kit (Applied Biosystems). The reverse transcription reaction was conducted at 25° C. for 10 minutes, 37° C. for 2 hours, and was finally kept at 4° C.

Primers and Probe Design

The fluorescently tagged Taqman primer sequences and specific probes were used (Taqman Gene Expression Assays) (Applied Biosystems) for eukaryote rRNA 18S, interferon-gamma (IFN-γ), interleukin 2 (IL-2), tumour necrosis factor alpha (TNF-α), interleukin 10 (IL-10) and inducible nitric oxide synthase (iNOS).

Quantitative Real-Time PCR

For the quantitative PCR, the TaqMan Universal Master Mix (Applied Biosystems) was used. The cDNA amplification was performed on 96-well plates (MJ Research, Inc.) on an Opticon 2 real-time system (MJ Research). The reaction was performed on a 25-μl final reaction mix composed of 1× Taqman Universal Master Mix, 1× TaqMan Gene Expression Assay Mix (0.9 μM of each primer and 0.25 μM for the probe), and 20 ng of cDNA dissolved in RNase- and DNase-free water.

The reaction conditions were the following: 2 min at 50° C., 10 min at 95° C. and 40 15-s cycles at 95° C. and 1 min at 60° C. Each sample was loaded in triplicate and, on each plate, the blank and the endogenous control were amplified on different wells.

The IL-2, IFN-γ, TNF-α, IL-10 and iNOS mRNA expression levels were quantified in relation to the rRNA 18S constitutive gene.

Histopathology, Inflammation and Demyelination

Histological evaluation of the brain and spinal cord sections included in paraffin was conducted. The sections were stained with hematoxylin-eosin (HE) and Luxol fast-blue in order to be able to assess the tissues' inflammation and demyelination. 24-30 sagital sections were examined for each rat. The blind semi-quantitative histological evaluation of inflammation and demyelination was conducted as previously described [Villoslada, P., et al., J. Exp Med, 2000. 191 (10): 1799-806].

Immunohistochemistry

The immunohistochemical procedures were conducted on 10-μl m brain and medulla sections included in paraffin. The endogenous peroxidase activity was deactivated by means of 0.3% $H_2O_2$ in methanol for 20 min.

The sections were incubated for 30 min in PBS with 0.5% Tween® 20 and 10% goat or horse serum (Vector Laboratorios) and for 2 hours in PBS with 0.5% Tween® 20 and the primary antibodies in the following dilutions: rabbit antiglial fibrillary acid polyclonal anti-protein antibody (GFAP), 1:1,000 (Dakocytomation); mouse beta-amyloid precursor anti-protein antibody (APP), 1:100 (Zymed Laboratorios); mouse anti-IgA antibody (OX-6), 1:200 (Serotec); rat anti-CD8 antibody, 1:250 (Serotec); type II anti-iNOS antibody, 1:250 (Serotec); rat anti-CD68 antibody (ED1), 1:200 (Serotec) and rat anti-CD43 antibody (W3/13), 1:50 (Serotec). Subsequently, the sections were washed with PBS and incubated for 45 min at room temperature with the appropriate biotinylated secondary IgG antibody (1:100 in PBS; Vector Laboratorios), followed by several washes in PBS/Tween® and a 45-min incubation at room temperature with the avidin-biotin peroxidase complex (ABC, Vector Laboratorios).

Following the washes in PBS/Tween®, the immunoreactivity was revealed using 0.5 mg/ml of 3,3'-diaminobenzidine tetrahydrochlorate (DAB; Sigma). The immunoreaction specificity was determined by incubating the sections without the primary antibody. The images were obtained using an optic microscope.

Lymphocyte Proliferation Assay

The splenocytes were purified by means of Ficoll Hypaque density centrifugation starting from the rats with EAE and non-immunised rats. The lymphocite proliferation assay was conducted in the same manner as previously described [Villoslada, P., et al., J. Exp Med, 2000. 191 (10):1799-806].

Briefly, the splenocytes were placed in culture at a concentration of $2 \times 10^6$/ml in RPMI 1640 medium supplemented with 10% fetal bovine serum and penicillin/streptomycin, in the presence or absence of phytohemagglutinin (PHA, 5 μg/ml), MBP (10 μg/ml), MTA (100 μM) and DMSO. The cultures were incubated for 5 days in 96-well round-base plates (0.2 ml/well) at 37° C. The wells were struck with 0.5 μCi [$^3$H]TdR for 18 hours. The reading was performed using a liquid scintillation counter. The results were expressed as the mean stimulation index of the triplicate determinations.

Statistical Analysis

The statistical comparison was performed using the Mann-Whitney two-tail test and survival curves. $p<0.05$ values are considered to be significant differences. The statistical evaluation was performed using the SPSS 11.0 statistics programme.

II. Results

Effect of MTA on the Development of the MS Outbreak Model (Acute EAE) in Lewis Rats Immunised with MBP Starting on the same day of the immunisation, the Lewis rats were randomly assigned to the group treated with MTA or the placebo group, and both of them were subject to intraperitoneal (i.p.) administration on a daily basis. All the animals receiving the placebo treatment except for one developed the neurological symptoms of EAE, consisting of progressive weight loss, lack of strength on the tail and hind leg paralysis or moderate or serious paraplegia. The first neurological symptoms were observed on day 12, with a mean disease onset day of 13.6±1.2 (n=21). The maximum score achieved by the individual animals during the course of the experiment was 1.48±1 (Table 1).

TABLE 1

EAE Score

| Treatment | Number of rats | EAE Incidence | Onset of EAE (days) | Max. EAE Score | Cumulative EAE Score |
|---|---|---|---|---|---|
| MTA | 14 | 4/14 (28.57%) | 15 ± 1.2 | 0.14 ± 0.23 | 2 ± 0.07 |
| Placebo | 21 | 20/21 (95.23%)[a] | 13.6 ± 1.2 | 1.48 ± 1[a] | 83.5 ± 0.65[a] |

Figure 1:
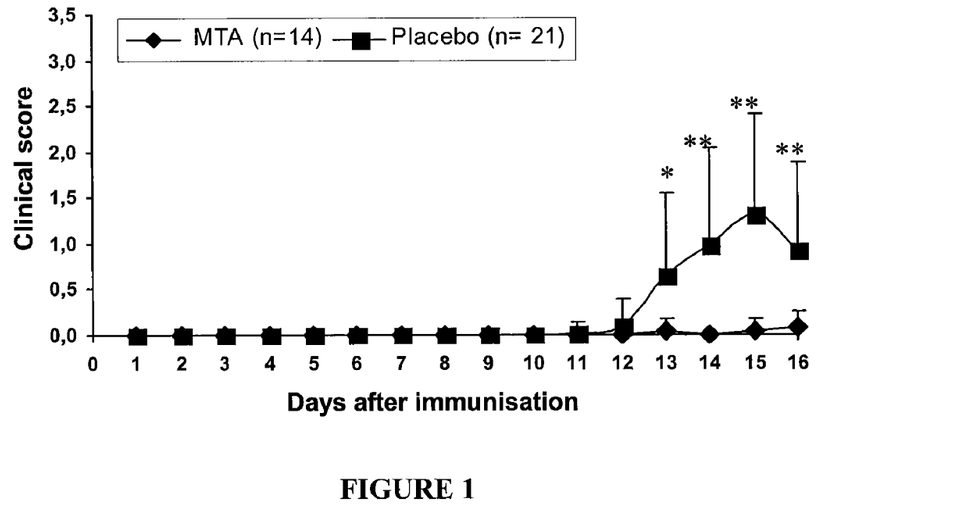
FIG. 1 is an illustrative graph of the induction of EAE in Lewis rats immunised with guinea pig $MBP_{68-82}$. The mean daily clinical score +S.E.M. is shown for each group of rats, where (*) means the statistically significant difference at $p<0.05$ as compared to treatment with MTA, and (**) means the statistically significant difference at $p<0.005$ as compared to treatment with MTA. The data are collected from 3 individual experiments.

[a]statistically significant difference at $p < 0.005$ as compared to treatment with MTA On the contrary, those animals that were treated with MTA either did not exhibit any clinical signs or else showed a strong attenuation during the course of the disease. In those treated animals that developed clinical symptoms, the onset of the disease was delayed by comparison with the placebo group (day 15±1.2). The maximum clinical scores observed were significantly lower than those of the placebo group (0.14±0.23) (Table 1) (FIG. 1).

Figure 2:
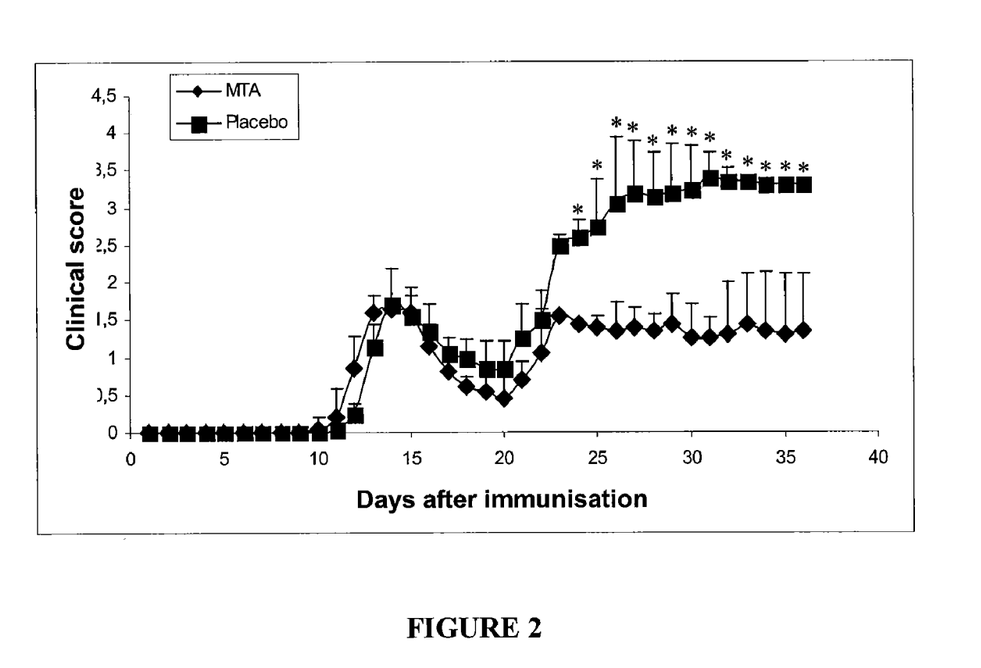
FIG. 2 is an illustrative graph of the induction of chronic-recurrent EAE in DA rats immunised with rMOG. The mean daily clinical score +S.E.M. is shown for each group of rats, where (*) means the statistically significant difference at $p<0.005$ as compared to treatment with MTA.
Figure 3:
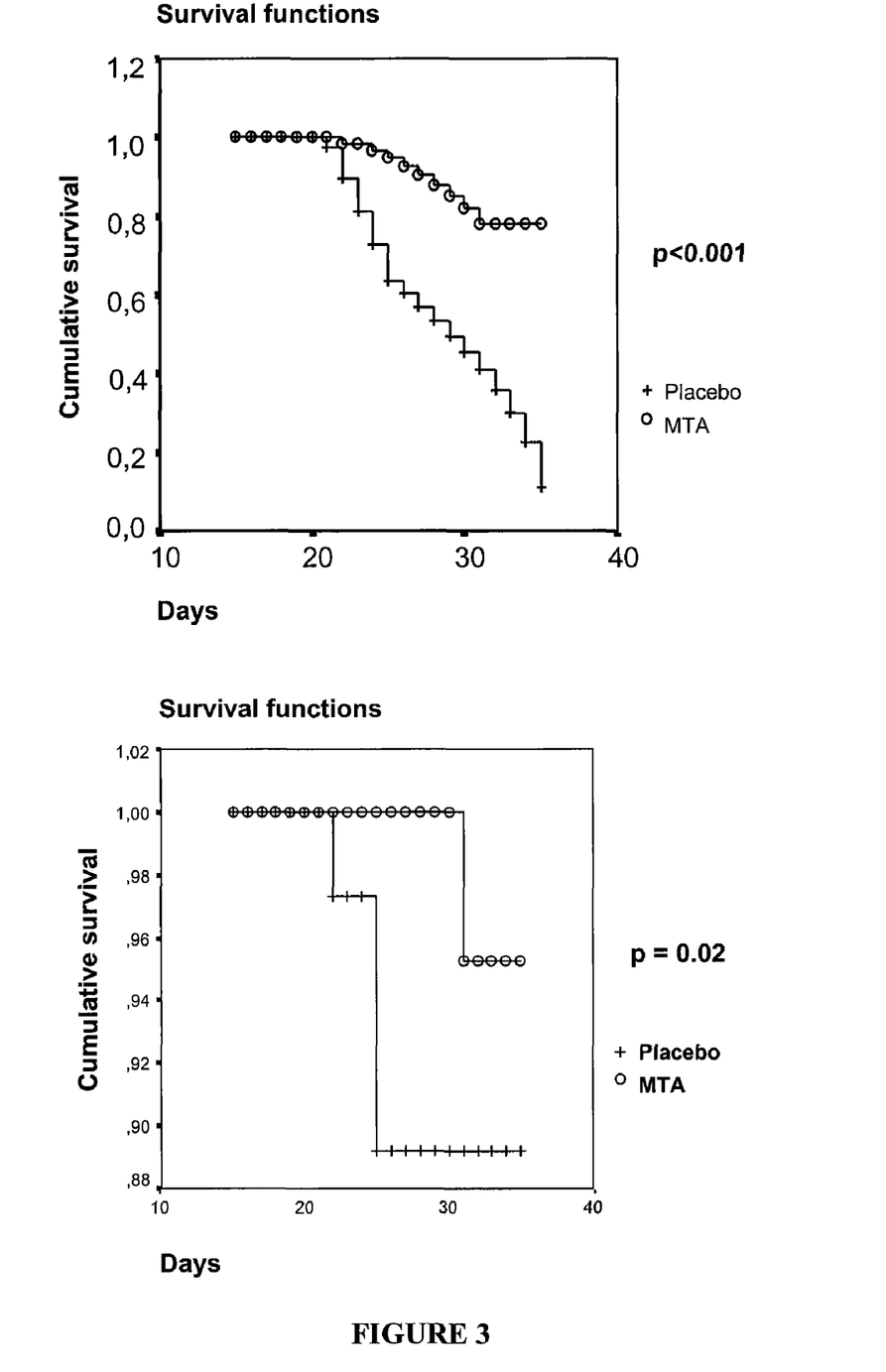
FIG. 3 is an illustrative graph of the survival curve for DA rats immunised with MOG until they reach moderate disability (score=3.5) ($p<0.001$ by the Breslow test) [FIG. 3A], and the survival curve for DA rats immunised with MOG until they reach exitus (score=5) ($p=0.02$ by the Breslow test) [FIG. 3B].

Effect of MTA on the Development of the MS Model (CR-EAE) in DA Rats Immunised with MOG After going through the first outbreak [5 days after the onset of the first outbreak (approximately towards day 15-18 after immunisation)], the DA rats were randomly assigned to the group treated with MTA or the placebo group, and both received intraperitoneal (i.p.) administration on a daily basis. All the animals developed a second outbreak of the disease, but the differences between both groups in the neurological symptoms, the severity of the second outbreak and survival were significant. In those animals that were treated with MTA, the onset of the second outbreak was delayed by comparison with the placebo group (day 23.4±6.54), although the differences were not significant. The maximum clinical scores observed were lower than for the placebo group (2.7±1.75) (Table 2) (FIG. 2). Furthermore, the survival rate was significantly higher in the group that was treated with MTA (FIG. 3).

TABLE 2

EAE Score

| Treatment | Number of rats | Incidence 2nd outbreak | Onset (days) 2nd outbreak | Max. EAE Score | Cumulative EAE Score |
|---|---|---|---|---|---|
| MTA | 10 | 10/10 | 26 ± 6 | 1.8 ± 1.5 | 23 ± 20 |
| Placebo | 10 | 10/10 | 21 ± 3* | 3.6 ± 1.5* | 50 ± 20* |

Figure 4:
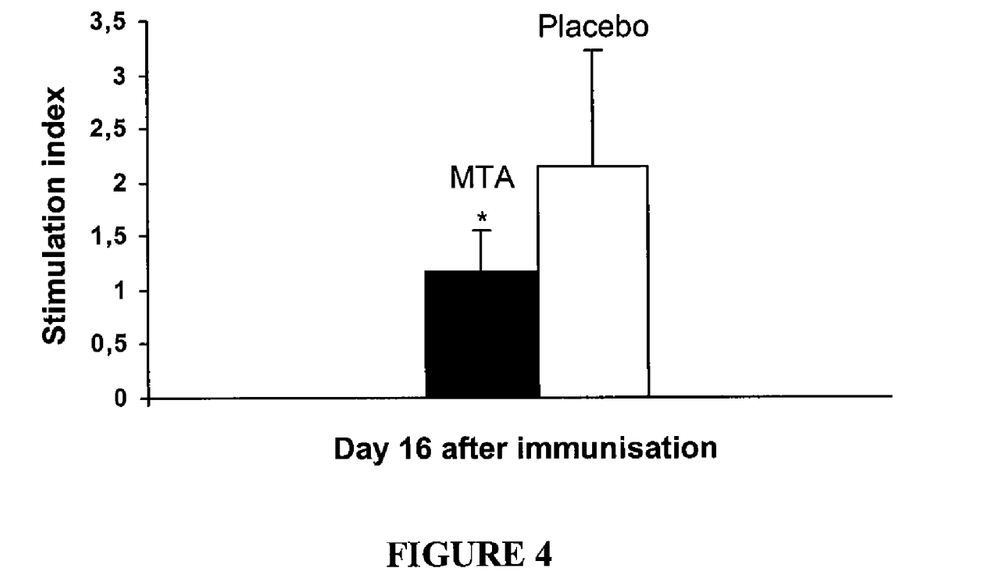
FIG. 4 is a bar diagram which shows the MBP-specific T-lymphocyte response in Lewis rats immunised with MBP on day 16 after immunisation. The results are expressed as the mean stimulation index, where (*) means the statistically significant difference at $p<0.05$, as compared to treatment with a placebo.

*statistically significant difference at $p < 0.05$ as compared to treatment with MTA MTA Inhibits Lymphocyte Proliferation In order to determine whether treatment with MTA modified the peripheral immune system's response to the antigen used in the immunisation, the MBP-induced proliferation responses were measured in splenocytes of animals treated with MTA and placebo (in Lewis rats). The MBP-specific proliferation response was significantly lower in those animals treated with MTA, as can be seen in FIG. 4. Thus, the stimulation index of the group treated with MTA was 1.18±0.4 and that of the placebo group was 2.13±1.09, which indicates that the T cell responses are affected by treatment with MTA. Therefore, it is observed that MTA inhibits the MBP-specific lymphocyte activation, which points to its immunomodulatory effect.

MTA Modifies the Expression of Cytokines and Pro-Inflammatory Mediators

Figure 5:
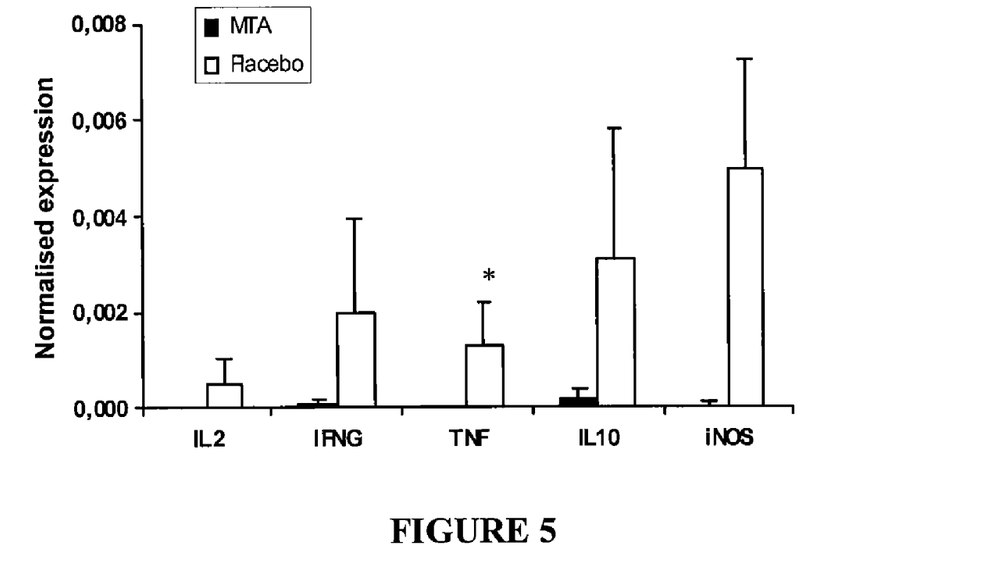
FIG. 5 is a bar diagram which shows an IL-2, IFN-γ, TNF, IL-10 and iNOS mRNA expression pattern in the splenocytes of rats with EAE. The data are expressed as relative to the level of the 18S rRNA constitutive gene, where (*) means the significant difference at $p<0.05$ as compared to MTA.

It was assessed whether MTA had the capacity to modify the expression of cytokines and other pro-inflammatory mediators. The IL-2, IFN-γ, TNF-α, IL-10 and iNOS gene expression was analysed by means of quantitative real-time PCR (RT-PCR). The relative mRNA levels of these isolated genes of splenocytes from placebo Lewis rats and rats treated with MTA are shown in FIG. 5. The mRNA expression of said cytokines was lower by comparison with the animals in the placebo group, although only the TNF levels were significantly different.

Histological Analysis

Figure 6:
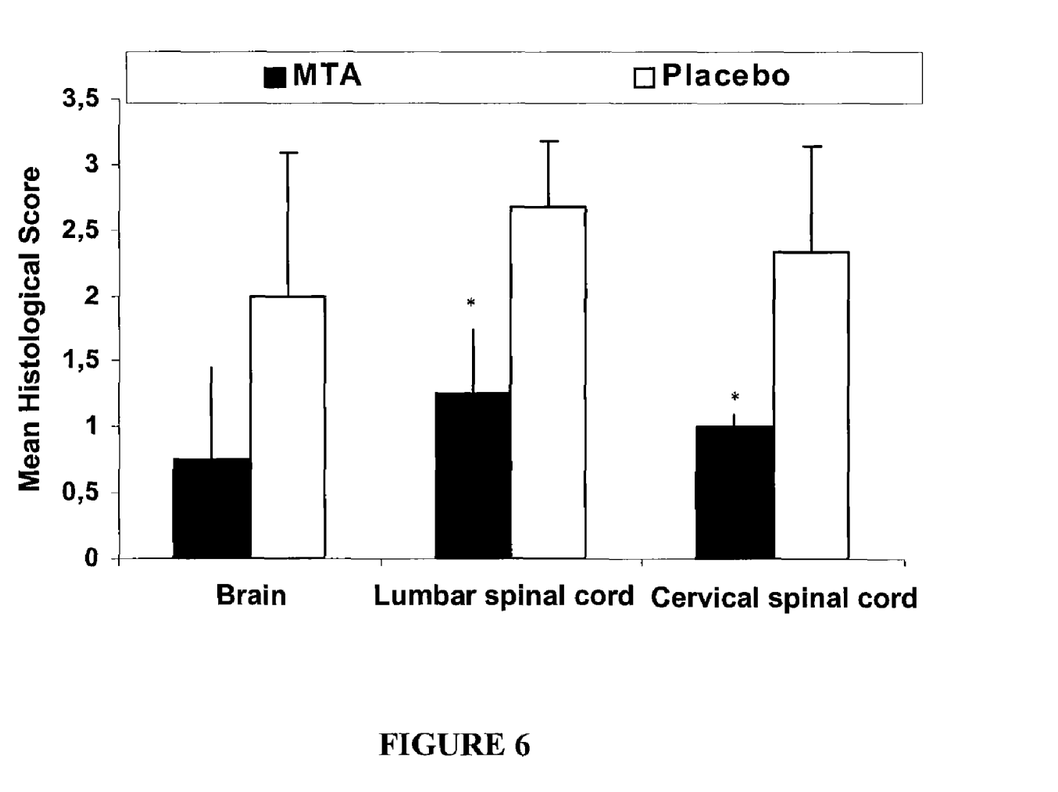
FIG. 6 is a bar diagram which shows the histological scores of the inflammatory and demyelinating lesions, where (*) means the statistically significant difference at $p<0.05$ as compared to MTA.

The neuropathological evaluation confirmed the observed clinical protection. Examination of the spinal cord and the brains of the placebo animals showed multiple inflammation foci. Inflammatory lesions were found in both the white and grey matter of the cervical, thoracic and lumbar spinal cord, and the brain. In those rats that were treated with MTA, both the number and the size of the inflammatory infiltrates was found to be lower (FIG. 6). There were significant differences between the placebo animals and those treated with MTA in terms of both the severity and the central nervous system (CNS) regions affected. Treatment with MTA inhibits the development of inflammatory EAE in Lewis rats immunised with MBP. Immunohistochemical staining revealed the presence of several cell types in the inflammatory infiltrates, including macrophages and activated microglial cells (ED1), T lymphocytes (W3/13) and B lymphocytes (OX-6). The number of positive ED1 and W3/13 cells was higher in the placebo group, whilst both groups of animals showed the same proportions of positive OX-6 cells. The stains for APP and iNOS were found to be at very low detection levels in both groups.

III. Discussion

EAE is an autoimmunity model which is critically dependent on T cell activation. The MBP- or MOG-specific CD4+ cells, two CNS autoantigens, may induce EAE. Lymphocyte activation is necessary for initial entry into the CNS. Recognition of the antigen by the CD4+ T cells requires the expression of class II MHC molecules in the antigen-presenting cells (APC). Under normal conditions, the CNS has a very low expression of these molecules. Through the secretion of IFN-γ, a potent stimulant for the expression of class II MHC molecules in antigen-presenting cells residing in the CNS, such as microglial cells and astrocytes, the Th 1 cells recognise myelin. Therefore, a treatment that interferes with T lymphocyte activation may inhibit the development of autoimmune diseases, such as EAE.

The decrease in the MBP-specific proliferation response in Lewis rats immunised with MBP and treated with MTA indicates that methylation is a critical step in lymphocyte activation. The selective inhibition of reactive T cells against MBP prevents the activation of autoreactive lymphocytes and the entry of the inflammatory cells into the CNS through the production of cytokines and/or chemokines. This leads, as a consequence, to a less severe disease, as can be seen in the EAE clinical scale and the histological analyses of those animals treated with MTA. The cumulative EAE scale in the group that was treated with MTA is significantly lower than in the placebo group and the histological analyses show that the number of inflammatory lesions is considerably reduced.

In addition to MTA's preventive effect on the development of autoimmunity observed in EAE prevention in Lewis rats, it has been observed that MTA also has a healing effect on chronic autoimmunity. Treatment with MTA improved the clinical symptoms and survival when the disease had already started (after the first outbreak), as has been verified in the EAE model with DA rats immunised with MOG. This aspect is critically significant in medical terms, since in practise immunomodulatory treatments may be used when the disease has already begun, without it being possible at the moment to perform preventive treatments, since there are no pre-symptomatic markers.

The cytokines produced by the T cells may significantly affect the course of the disease. As can be seen in FIG. 5, lower levels of cytokine expression were found in those rats that were treated with MTA. One of the characteristics of EAE is the activation of iNOS expression in various cell types. The inventors observed that iNOS expression was lower in the spleens of rats that were treated with MTA. TNF is a cytokine that has been recognised as a central mediator in systemic inflammation and which, moreover, contributes to the activation of iNOS gene expression. In this EAE model (CR-EAE), it has been observed that MTA also reduces TNF-α levels. IL-2 is a key cytokine in T-dependent immune responses due to its potent activity as a growth factor for T cells. The results obtained show that MTA reduces the production of lymphocyte IL-2 by inhibiting specific T-cell activation. Furthermore, this molecule is capable of decreasing the production of IFN-γ. All these MTA effects indicate that it is capable of modifying the balance of cytokines towards a more anti-inflammatory profile.

In conclusion, the studies conducted demonstrate that MTA prevents against autoimmunity in the EAE model in Lewis rats immunised with MBP (acute EAE) and modifies and improves, i.e. exerts a therapeutic effect on, the disease in the chronic EAE model in DA rats immunised with rMOG (CR-EAE). The mechanism responsible for these protective effects would be the inhibition of MBP- or MOG-specific T cell activation, although other regulatory routes may be participating in the protection. These findings open the way for a new potential treatment of autoimmune diseases and transplant rejection by using a drug that is easy to synthesise, effective and with few secondary effects, which would represent significant progress in treating these diseases.

The invention claimed is:

1. A method for the treatment of an autoimmune disease in an individual in need thereof suffering from an autoimmune disease, wherein said autoimmune disease is Multiple Sclerosis (MS), said method comprising administering to said individual a therapeutically effective quantity of an immunomodulatory agent, said agent comprising 5'-methylthioadenosine (MTA) or a pharmaceutically acceptable salt thereof.

2. The method according to claim 1, wherein said method delays the onset of outbreaks in an individual suffering from MS.

3. The method according to claim 1, wherein said mode of administering said agent is selected from the group consisting of oral, subcutaneous, intraperitoneal and intravenous administration.

4. The method according to claim 1, wherein said method delays the progression of MS (progressive phase) in an individual suffering from MS.

5. The method according to claim 1, further comprising wherein said agent is administered in combination with interferon-beta (IFN-β).

6. The method according to claim 5, wherein said interferon-beta (IFN-β) is administered in the form of a separate composition intended for simultaneous administration with said immunomodulatory agent.

7. The method according to claim 5, wherein said interferon-beta (IFN-β) is administered in the form of a separate composition intended for non-simultaneous administration with said immunomodulatory agent.

* * * * *